(12) United States Patent
Kritzler

(10) Patent No.: US 10,010,072 B2
(45) Date of Patent: Jul. 3, 2018

(54) VIRICIDAL COMPOSITION

(75) Inventor: Steve Kritzler, Cronulla (AU)

(73) Assignee: Novapharm Research (Australia) Pty Ltd., Roseberry, New South Wales (AU)

( * ) Notice: Subject to any disclaimer, the term of this patent is extended or adjusted under 35 U.S.C. 154(b) by 0 days.

(21) Appl. No.: 12/808,210

(22) PCT Filed: Dec. 17, 2008

(86) PCT No.: PCT/AU2008/001860
§ 371 (c)(1),
(2), (4) Date: Jun. 15, 2010

(87) PCT Pub. No.: WO2009/076718
PCT Pub. Date: Jun. 25, 2009

(65) Prior Publication Data
US 2010/0260865 A1   Oct. 14, 2010

(30) Foreign Application Priority Data
Dec. 17, 2007   (AU) ................. 2007906914

(51) Int. Cl.
| A01N 31/02 | (2006.01) |
| A01N 33/12 | (2006.01) |
| A01N 59/00 | (2006.01) |
| A01N 31/16 | (2006.01) |
| A01N 25/02 | (2006.01) |
| A01N 25/10 | (2006.01) |

(52) U.S. Cl.
CPC .......... *A01N 31/16* (2013.01); *A01N 31/02* (2013.01); *A01N 33/12* (2013.01); *A01N 59/00* (2013.01); *A01N 25/02* (2013.01); *A01N 25/10* (2013.01)

(58) Field of Classification Search
CPC ........ A01N 25/02; A01N 31/00; A01N 33/12; A01N 59/00; A01N 31/02
USPC ................. 424/616, 613; 514/642, 643, 738
See application file for complete search history.

(56) References Cited

U.S. PATENT DOCUMENTS

| 4,320,102 | A | * | 3/1982 | Dalton, Jr. ............ C01B 15/037 423/273 |
| 4,477,438 | A | * | 10/1984 | Willcockson .......... A01N 59/00 252/389.52 |
| 4,900,721 | A | | 2/1990 | Bansemir et al. |
| 5,780,064 | A | * | 7/1998 | Meisters et al. ............... 424/616 |
| 6,080,417 | A | * | 6/2000 | Kramer et al. ............... 424/405 |
| 6,096,349 | A | | 8/2000 | Petri et al. |
| 6,146,651 | A | | 11/2000 | Kritzler |
| 6,566,574 | B1 | | 5/2003 | Tadros et al. |
| 7,888,404 | B2 | * | 2/2011 | Kritzler ................. A01N 33/12 523/122 |
| 2003/0100465 | A1 | * | 5/2003 | Kilkenny et al. ............. 510/384 |
| 2005/0115197 | A1 | | 6/2005 | Meyers et al. |
| 2005/0281757 | A1 | | 12/2005 | Ibrahim et al. |
| 2007/0140993 | A1 | | 6/2007 | Evison |
| 2007/0178055 | A1 | | 8/2007 | Buch et al. |
| 2007/0227557 | A1 | * | 10/2007 | Ohlhausen ........... C09D 183/08 134/4 |
| 2008/0175811 | A1 | | 7/2008 | Kritzler |
| 2009/0010970 | A1 | | 1/2009 | Velada |

FOREIGN PATENT DOCUMENTS

| DE | 10 2004 020 892 A1 | 11/2005 |
| EP | 1393629 A1 | 3/2004 |
| EP | 1 826 236 A1 | 8/2007 |
| JP | S62-292709 | 12/1987 |
| JP | H11-504629 | 4/1999 |
| JP | 2001-503768 | 3/2001 |
| JP | 2001-503770 | 3/2001 |
| JP | 2004-501731 | 1/2004 |
| JP | 2007-523138 | 8/2007 |
| JP | 2007-531771 | 11/2007 |
| JP | 2007-332322 | 12/2007 |
| WO | WO 96/33748 A1 * | 10/1996 |
| WO | WO 97/34834 A1 | 9/1997 |
| WO | WO-98/20735 A1 | 5/1998 |
| WO | 99/66961 | 12/1999 |
| WO | WO 01/65939 A1 | 9/2001 |
| WO | WO-02/02192 A1 | 1/2002 |
| WO | 2005/055963 A2 | 6/2005 |

(Continued)

OTHER PUBLICATIONS

Bruce Gamage, et al., "Selection and Use of Disinfectants", BC Centre for Disease Control, BCCDC Laboratory Services, 2003, obtained from the internet on Mar. 14, 2012 at http://www.bccdc.ca/NR/rdonlyres/EAA94ACF-02A9-4CF0-BE47-3F5817A25669/0/InfectionControl_GF_DisinfectntSelectnGuidelines_nov0503.pdf.*

Gerald Mcdonnell and A. Denver Russell, "Antiseptics and Disinfectants: Activity, Action, and Resistance", Clinical Microbiology Reviews, Jan. 1999, vol. 12, No. 1, p. 147-179.*

International Search Report for PCT/AU2008/001860 dated Mar. 18, 2009.

(Continued)

Primary Examiner — John Pak
Assistant Examiner — Nathan W Schlientz
(74) Attorney, Agent, or Firm — Nixon Peabody LLP; Jeffrey L. Costellia

(57) ABSTRACT

A non-staining composition which is bactericidal, fungicidal and viricidal when applied, comprising in combination; an iodine free bactericide and/or fungicide having a residual efficacy lasting longer than 3 hours on surfaces against bacteria and fungi and a peroxide. A carrier may also be present. The bactericide and/or fungicide may be for example triclosan or a quaternary ammonium compound, or preferably a PVP-phenolic biocide complex (eg PVP-triclosan) or PVAlc/quaternary ammonium compound complex (eg PVP/benzalkonium chloride). The peroxide may be hydrogen peroxide.

18 Claims, No Drawings

(56) References Cited

FOREIGN PATENT DOCUMENTS

| | | |
|---|---|---|
| WO | 2005/089100 A2 | 9/2005 |
| WO | WO 2006/081617 A1 * | 8/2006 |
| WO | WO-2006/107334 A1 | 10/2006 |
| WO | WO 2006/122345 A1 * | 11/2006 |
| WO | WO-2006/122345 A1 | 11/2006 |
| WO | 2007/038855 A1 | 4/2007 |

OTHER PUBLICATIONS

"Study on Screening of Formula of Hydrogen Peroxide Foam Disinfectant", Chinese Journal of Disinfection, 2006, 23 (5), 4 pages.

European Examination Report corresponding to European Patent Application No. 08862562.9, European Patent Office; dated Nov. 11, 2016; (4 pages).

* cited by examiner

VIRICIDAL COMPOSITION

FIELD OF THE INVENTION

The present invention relates to a method and composition for treating a surface with a viricidal solution. The solution may be applicable to animate or inanimate surfaces. In the case of inanimate surfaces the solution (which may eventually dry to a clear, adherent, long acting biocidal surface coating) kills bacteria, fungi, and viruses, on a surface to which it is applied and in preferred embodiments renders the surface resistant against re-infestation by fungi and bacteria. On animate surfaces the solution may be left in place to dry as described above for inanimate surfaces or may be rinsed from the surface after having achieved the same spectrum of kill of infectious biological agents.

The composition is applicable to inanimate surfaces such as hospital operating theatre work surfaces, kitchen work benches, and bathrooms. The composition may also be formulated as preparations for skin treatments and hand rubs.

BACKGROUND OF THE INVENTION

Any discussion of the prior art throughout the specification should in no way be considered as an admission that such prior art is widely known or forms part of common general knowledge in the field.

A number of compositions are known which may be applied to skin or inanimate surfaces to confer bactericidal or fungicidal properties or both. Many of these are effective against selected organisms only, for example gram positive bacteria but not gram negative bacteria, but the better products are of broad spectrum effectiveness against bacteria and fungi. In our patent application PCT/AU96/00224 (published as WO96/033748) we described a polyvinyl pyrrolidone ("PVP")-triclosan complex which is effective against a broad spectrum of bacteria and fungi.

In another patent application PCT/AU2006/000130 (published as WO06/081617) we described a poly vinyl alcohol (PVAlc)-quaternary ammonium compound complex which is effective against a broad spectrum of bacteria and fungi.

However the only known safe polymer/biocide complexes which are effective against viruses incorporate iodine. These complexes, such as are formed by iodine and ethoxylated non-ionic surfactants or iodine and polyvinylpyrrolidone, are very dark brown in colour and stain both inanimate surfaces and skin and clothing resulting in them being largely unpopular. Furthermore the active biocide in the complexes is iodine, a very chemically active substance. This high degree of reactivity leads to short residual activity since the iodine is sacrificially active against not only micro organisms and viruses but also against all proteins and many other substances. It would be highly desirable to provide a composition which was not only bactericidal and fungicidal but which was also viricidal, non staining and safe.

In addition many of the known compositions such as the iodine complexes described above are only efficacious for a matter of a one or two hours. It would be desirable to provide a composition which had a residual efficacy for days or weeks. Desirably the composition should be non staining, clear or virtually invisible when applied to a surface, should be adherent, and durable.

OBJECT OF THE INVENTION

It is an object of this invention to provide a composition which avoids or ameliorates at least some of the disadvantages of the prior art.

It is an object of preferred embodiments to be able to kill viruses, bacteria and fungi on surfaces in chambers such as operating theatres, wards of hospitals, cold rooms, refrigerators, vans, sea containers, factory areas where disinfection is a requirement and also on skin and preferably to do so by application of a single composition.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

BRIEF STATEMENT OF INVENTION

According to a first aspect the present invention provides a non staining composition which is bactericidal, fungicidal and viricidal when applied comprising in combination;
(1) an iodine free bactericide and/or fungicide having a residual efficacy lasting longer than 3 hours on surfaces against bacteria and fungi; and
(2) a peroxide.

In preferred embodiments according to the first aspect the bactericide and/or fungicide is triclosan or is a suitable quaternary ammonium compound. In highly preferred embodiments of compositions formulated for used on inanimate surfaces the residual efficacy lasts for longer than 12 hours and preferably for longer than 7 days.

Preferably the composition further includes (3) a carrier which on evaporation leaves a disinfected inanimate or animate surface.

According to a second aspect the present invention provides a non staining composition which is bactericidal, fungicidal and viricidal when applied comprising in combination;
(1) an iodine free bactericide and/or fungicide having a residual efficacy lasting longer than 12 hours on inanimate surfaces against bacteria and fungi;
(2) a peroxide; and
(3) a carrier which on evaporation leaves a disinfected inanimate or animate surface.

In preferred embodiments, compositions according to the first or second aspect are suitable for use on inanimate surfaces, and may be formulated to leave clear dry and adherent films on the surface and which remain free of viruses, bacteria and fungi for many hours. In other embodiments compositions according to the invention are formulated for use on animate surfaces such as skin and in such cases may be formulated for example as aqueous hand washes or alcoholic hand rubs which retain residual biocidal efficacy against bacteria and fungi (not withstanding rinsing after hand washing)

In one highly preferred embodiment according to the second aspect the full spectrum bactericide is a complex formed from polyvinylpyrolidone ("PVP") with a phenolic biocide. A highly preferred complex is a PVP-Triclosan complex which has activity against gram positive and gram negative bacteria when appropriately formulated and which is effective for days if not weeks, but is not viricidal. Copolymers of PVP may be substituted for PVP in the complex but this of itself does not confer viricidal activity. As herein used the term "PVP" includes both PVP and PVP copolymers Preferably the ratio of PVP:phenolic biocide is 1:0.05 to 0.05:1 (w/w). Preferably the phenolic biocide is present in an amount of 0.1 to 1%. Preferably the PVP is present in an amount of PVP 0.2 to 15% w/w.

In a second highly preferred embodiment a poly vinyl alcohol ("PVAlc")-quaternary ammonium compound complex is substituted for a PVP complex. The PVAlc may be of any degree of hydrolysis and the complex may be formed with any suitable biocidal aromatic or aliphatic quaternary ammonium compound.

Preferably the ratio of PVAlc:benzalkonium chloride is in a range of from 1:0.05 to 1:1 (w/w) where a dry residue is required. Preferably the ratio of PVAlc:benzalkonium chloride is 1:1 or greater if a dry residue is not required. Preferably the ratio of PVAlc:benzalkonium chloride is 1:2 or if a dry residue is not required.

Preferably the quaternary ammonium compound is present in an amount of 0.2 to 12% (w/w). Preferably the PVAlc is present in an amount of 0.5 to 30% (w/w). Preferably the quaternary ammonium compound is benzalkonium chloride.

A preferred peroxide for use in the invention is hydrogen peroxide as a solution in water, desirably at an initial concentration of 15% at "in use" dilutions or less (based on 100% peroxide), preferably at an initial concentration of 5-7%, more preferably 6% on inanimate surfaces or less and more preferably on animate surfaces at a concentration of 3% or less. In one embodiment, the peroxide concentration is 1.0-3% (w/w). Hydrogen peroxide is known to be a strong oxidising agent and is difficult to formulate in combination with organic molecules such as the preferred bactericide and fungicides. It is especially surprising that a PVP-Triclosan complex can be maintained in the presence of a strong oxidising agent such as hydrogen peroxide. It is also well known that peroxides are unstable in the presence of amines and therefore surprising and unexpected that combination with a quaternary ammonium compound would be chemically stable.

Compositions according to the invention provide a fast acting viricidal effect. However in combination with the selected bactericide there is a residual efficacy which prevents re-colonization of a treated surface According to a third aspect the invention provides a composition comprising in combination a polyvinyl pyrrolidone-triclosan complex, hydrogen peroxide, and a carrier.

According to a fourth aspect the invention provides a composition comprising in combination a polyvinyl alcohol-quaternary ammonium compound complex, hydrogen peroxide, and a carrier.

The carrier may contain any suitable ingredients, including but not limited to alcohols (such as ethanol, propanol, isopropanol etc), glycols, water, fragrances, colourants etc.

The invention will now be more particularly described by way of example only with reference to particular examples.

Examples 1, 2,& 3 below are surface disinfectants. Example 4 is an aqueous hand antiseptic while example 5 is an alcoholic hand antiseptic.

In example 1 a polyvinyl alcohol ("PVAlc")-quaternary ammonium compound is employed as the bactericide and fungicide and 50% hydrogen peroxide solution is the peroxide. The carrier is water which in example 1 is optionally formulated with ethanol, a non-ionic surfactant (Teric164) and EDTA.

Example 1 PV Alcohol/Benzalkonium Chloride/Peroxide Surface Disinfectant

| | |
|---|---|
| Polyvinyl alcohol | 3.0% w/w |
| Benzalkonium chloride | 0.7%% w/w |
| Teric 164 | 1.0% w/w |
| Ethanol | 10.0% w/w |
| EDTA 4Na | 0.1% w/w |
| Hydrogen peroxide (50%) | 12.0% w/w |
| Water qs | 100.0% w/w |

The approximate ratios of PVAlc to Benzalkonium Chloride should be in a range of from 1:0.05 to a range of 1:1 w/w to achieve a dry residue but may be over 1:1 (e.g. 1:2) if this dry residue is not required.

The composition desirably contain from 0.5% to 30% w/w of Polyvinyl alcohol and from 0.2 to 12% w/w of benzalkonium chloride. The peroxide may be at any suitable concentration, but preferably less than 10% w/w (based on 100% peroxide. The example uses 12% of 50% peroxide). For antisepsis rather than disinfection the preferred concentration range of hydrogen peroxide is 1.0% to 3.0%.

It will be understood that PVAlc suitable for use in the invention may be of any degree of hydrolysis and preferably has a molecular weight in the 10 to 150 kDa range.

Examples 2 and 3 are surface disinfectants similar to example 1 but employing a PVP-triclosan bactericide or fungicide.

Example 2 PVP/Triclosan/Peroxide Surface Disinfectant

| | |
|---|---|
| PVP or its copolymers | 0.1% w/w |
| Triclosan | 0.05 w/w |
| Ethanol | 18.0% w/w |
| Non-ionic surfactant | 0.80% w/w |
| Hydrogen Peroxide (50%) | 12.0% w/w |
| Water qs | 100.0% w/w |

The approximate ratios of PVP to phenolic biocide, such as for example, PVP to Triclosan should be in a range of from 1:0.05 to a range of 0.05:1 w/w.

Example 3 PVP/Triclosan/Peroxide Surface Disinfectant

| | |
|---|---|
| PVP or its copolymers | 1.5% w/w |
| Triclosan | 0.2% w/w |
| Ethanol | 18.0% w/w |
| Non-ionic surfactant | 0.80% w/w |
| Hydrogen Peroxide (50%) | 12.0% w/w |
| Water qs | 100.0% w/w |

The approximate ratios of PVP to Triclosan should be in a range of from 1:0.05 to a range of 1:1, and preferably in a range of from 1:05 to 1:1 w/w The compositions of examples 2, 3 desirably contain from 0.2% to 15% w/w of PVP and from 0.1 to 1% w/w of phenolic biocide such as for example triclosan.

Example 4 PVP/Triclosan/Peroxide Hand Antiseptic—Aqueous

| | |
|---|---|
| Water qs | 100.0% |
| Viscosity Modifier | 1.00% w/w |
| Ethanol | 10.00% w/w |

-continued

| | |
|---|---|
| Propylene glycol | 3.00% w/w |
| Sodium laurylether sulphate | 5.00% w/w |
| Non-ionic surfactant | 2.00% w/w |
| Phenoxyethanol | 2.00% w/w |
| Perfume | 0.10% w/w |
| Phosphoric acid 10% | 1.80% w/w |
| Triclosan | 0.50% w/w |
| PVP or its copolymers | 0.50% w/w |
| Hydrogen peroxide | 3.00% w/w |

The ratios of PVP to Triclosan should be in the same range as 3 above.

Example 5 PVP/Triclosan/Peroxide Hand Antiseptic—Alcoholic

| | |
|---|---|
| PVP or its copolymers | 0.5 to 5.0% w/w |
| Triclosan | 0.50% w/w |
| Dipropylene glycol | 0.80% w/w |
| Viscosity modifier | 0.50% w/w |
| Ethanol | 60.00% w/w |
| Phenoxyethanol | 2.00% w/w |
| Perfume | 0.20% w/w |
| Blue #1(0.1% soln) | 0.30% w/w |
| Hydrogen Peroxide | 1.50% w/w |
| AMP 95 | 0.04% w/w |
| Water qs | 100.0% w/w |

Copolymers of PVP for example with vinyl acetates may be substituted for PVP in the PVP-triclosan complex. Although hydrogen peroxide solution is convenient to use other peroxides may be substituted.

Comparative Examples 6, 7, 8

These examples correspond to examples 1, 2, 3 respectively but with omission of the hydrogen peroxide.

Comparative Examples 9, 10

These examples correspond to examples 4, 5 respectively but with omission of the hydrogen peroxide.

The compositions were tested using the following test methods. Each of the tests is a pass/fail test for which the criteria for passage are defined in the method:—

Tests used for Formulations 1, 2, 3 and 6, 7, 8 which are surface disinfectants:

Test Methods:
Hard Surface Disinfectant:
Test 1. TGA Option B, dirty conditions

| | |
|---|---|
| S. aureus | NCTC 4163 |
| E. coli | NCTC 8196 |
| P. aeruginosa | NCTC 6749 |
| P. vulgaris | NCTC 4635 |

Bacterial counts should be $2\times10^8$ and $2\times10^9$ cfu per mL

The sample passes the test if there is no apparent growth in at least two out of the five recovery broths at 8 minutes & no apparent growth in at least two of the five recovery broths at 18 minutes on all three occasions, using all four organisms.

Test 2 Germicidal Spray test AOAC Official Method 961.02 (1995)

| Organism | Initial Count cfu/carrier | No. of tubes showing growth |
|---|---|---|
| S. aureus ATCC 6538 | $10^5$-$10^6$ | 0/10 |
| Ps. aeruginosa ATCC 15442 | $10^5$-$10^6$ | 0/10 |
| Sal. choleraesuis ATCC 10708 | $10^5$-$10^6$ | 0/10 |

Test 3 Standard Test Method for Efficacy of Virucidal Agents Intended for Inanimate Environmental Surfaces, ASTM E1053-97
Polio virus type 1, Chat strain, ATCC VR-192
Hepatitis A virus, HM-175 strain, ATCC VR-2093
Herpes simplex type 1, strain F (1), ATCC VR-33
Adenovirus type 2, aenoid 6 strain, ATCC VR-2
Titre $10^7$-$10^8$ infective units/ml
log reduction not less than 4
If toxicity of the product is high log reduction is not less than 3
Hand Wash Antiseptic:
In Vitro Test:
Test 4 Chemical Disinfectants And Antiseptics—Quantitative Suspension Test for the Evaluation of Basic Bactericidal Activity of Chemical Disinfectants and Antiseptics—Test Method and Requirements (Phase 1), EN 1040:2006
*Pseudomonas aeruginosa* ATCC 15442
*Staphylococcus aureus* ATCC 6538
Bacterial culture: between $1.5\times10^8$ to $5\times10^8$ cfu/ml
log reduction: >5
Test 5 Standard Test Method for Efficacy of Antimicrobial Agents Against Viruses in Suspension, ASTM E1052-96
Polio virus type 1, Chat strain, ATCC VR-192
Hepatitis A virus, HM-175 strain, ATCC VR-2093
Herpes simplex type 1, strain F (1), ATCC VR-33
Adenovirus type 2, aenoid 6 strain, ATCC VR-2
Titre $10^7$-$10^8$ infective units/ml
log reduction not less than 4
If toxicity of the product is high log reduction is not less than 3
Tests used for formulations 4, 5 and 9, 10 which are skin antiseptics:
In-Vivo Test:
Test 6 Chemical Disinfectants and Antiseptics—Hygienic Handwash—Test Method and Requirements (phase 2/step 2), EN 1499:1997
*E. coli* K12 NCTC 10538
Mean log prevalue should be more than 5
The mean log reduction must be significantly larger than that from soft soap.
Test 7 Chemical Disinfectants and Antiseptics—Hygienic Handrub—Test Method and Requirements (phase 2/step 2), EN 1500:1997
*E. coli* K12 NCTC 10538
Mean log prevalue should be more than 5
The mean log reduction of product shall not be significantly smaller than that of the reference propan-2-ol
It will be understood that various virus test methods are used by regulators to validate viricidal activity for skin antiseptics however these methods are in vitro, not in vivo. Such a test method is ASTM E 1052-96.

Results:

TABLE 1 test results for examples of surface disinfectants 1-3 and 6-8

| Test | Ex. 1 | Ex. 2 | Ex. 3 | Ex. 6 | Ex. 7 | Ex. 8 |
| --- | --- | --- | --- | --- | --- | --- |
| Test 1 | pass | pass | pass | pass | pass | pass |
| Test 2 | pass | pass | pass | pass | pass | pass |
| Test 3 | pass | pass | pass | fail | fail | fail |

TABLE 2 test results for examples skin antiseptics 4-5 and 9-10

| Test | Ex. 4 | Ex. 5 | Ex. 9 | Ex. 10 |
| --- | --- | --- | --- | --- |
| Test 4 | pass | pass | pass | pass |
| Test 5 | pass | pass | fail | fail |
| Test 6 | pass | pass | pass | pass |
| Test 7 | pass | pass | pass | pass |

Some further compositions according to the invention will now be described by way of example only

Example 11 PVP/Triclosan/Peroxide Hand Antiseptic—Aqueous (This example is similar to example 4 but including 1.00% urea as a peroxidase inhibitor)

| | |
| --- | --- |
| Water qs | 100.0% |
| Viscosity Modifier | 1.00% w/w |
| Ethanol | 10.00% w/w |
| Propylene glycol | 3.00% w/w |
| Sodium laurylethersulphate | 5.00% w/w |
| Non-ionic surfactant | 2.00% w/w |
| Urea | 1.00% w/w |
| Phenoxyethanol | 2.00% w/w |
| Perfume | 0.10% w/w |
| Phosphoric acid 10% | 1.80% w/w |
| Triclosan | 0.50% w/w |
| PVP or its copolymers | 0.50% w/w |
| Hydrogen peroxide | 3.00% w/w |

Example 12 PVP/Triclosan/Peroxide Hand Antiseptic—Alcoholic (As for example 11 but including 0.50% urea as a peroxidase inhibitor))

| | |
| --- | --- |
| PVP or its copolymers | 0.5 to 5.0% w/w |
| Triclosan | 0.50% w/w |
| Dipropylene glycol | 0.80% w/w |
| Viscosity modifier | 0.50% w/w |
| Ethanol | 60.00% w/w Steve to check |
| Phenoxyethanol | 2.00% w/w |
| Perfume | 0.20% w/w |
| Blue #1(0.1% soln) | 0.30% w/w |
| Hydrogen Peroxide | 1.50% w/w |
| AMP 95 | 0.04% w/w |
| Urea | 0.50% w/w |
| Water qs | 100.0% w/w |

Example 13 Antiseptic Handwashing Quat and Peroxide

| | |
| --- | --- |
| Polyvinyl alcohol | 1.0% w/w |
| Benzalkonium chloride | 0.3%% w/w |
| Nonionic surfactant | 7.0% w/w |
| Ethanol | 10.0% w/w |
| EDTA 4Na | 0.1% w/w |
| Hydrogen peroxide (50%) | 6.0% w/w |
| Water qs | 100.0% w/w |

Example 14 Antiseptic Alcoholic Handrub

| | |
| --- | --- |
| Polyvinyl alcohol | 0.5% w/w |
| Benzalkonium chloride | 0.2%% w/w |
| Non-ionic surfactant | 1.0% w/w |
| Ethanol | 60.0% w/w |
| Hydrogen peroxide (50%) | 3.0% w/w |
| Water qs | 100.0% w/w |

Example 15 PVP/Triclosan/Peroxide Hand Antiseptic—Aqueous

This formulation is similar to that of example 3 but omits PVP

| | |
| --- | --- |
| Water qs | 100.0% |
| Viscosity Modifier | 1.00% w/w |
| Ethanol | 10.00% w/w |
| Propylene glycol | 3.00% w/w |
| Sodium laurylether sulphate | 5.00% w/w |
| Non-ionic surfactant | 2.00% w/w |
| Phenoxyethanol | 2.00% w/w |
| Perfume | 0.10% w/w |
| Phosphoric acid 10% | 1.80% w/w |
| Triclosan | 0.50% w/w |
| Hydrogen peroxide | 3.00% w/w |

The triclosan hard surface and skin formulations do not leave an adherent film without PVP although the quat formulations do leave adherent films without PVAlc. It will be understood that although the handwashes do not leave adherent films because they are rinsed after washing, the triclosan leaves residual efficacy by dissolving into skin lipids. The quat handwashes leave residual efficacy by being substantive to the skin by virtue of cationic attraction to the protein.

Those skilled in the art will appreciate from the teaching hereof that other peroxidase inhibitors for example, alcohols and especially ethyl alcohol, or halogen salts at suitable concentrations may be used to inhibit the enzymes in skin which tend to breakdown peroxides.

As will be apparent to those skilled in the art from the teaching hereof formulations according to the invention can be varied in respect of solvents employed, surfactants and other formulation aids included. Any suitable phenolic biocide may be substituted for Triclosan in the preferred complex and other suitable quats may be substituted for those herein exemplified.

The claims defining the invention are as follows:
1. A composition which is bactericidal, fungicidal and viricidal when applied consisting essentially of:

(1) an iodine free Poly Vinyl Alcohol (PVAlc) or its copolymers and a benzalkonium chloride;
(2) a peroxide, wherein the peroxide is present and in an amount not exceeding 7% w/w; and,
(3) a carrier consisting of water, an alcohol and optionally glycols, fragrances and colorants, which creates a film on a disinfected inanimate or animate surface on evaporation;
wherein said film has a residual efficacy lasting longer than 3 hours on surfaces against bacteria and fungi when dry.

2. A composition according to claim 1 wherein the peroxide is hydrogen peroxide.

3. A composition according to claim 1 wherein the composition has a residual efficacy lasting longer than 12 hours on inanimate surfaces against bacteria and fungi.

4. A composition according to claim 1 wherein the ratio of PVAlc:benzalkonium chloride is in a range of from 1:0.05 to 1:1 (w/w) where a dry residue is required.

5. A composition according to claim 1 wherein the ratio of PVAlc:benzalkonium chloride is 1:1 or greater if a dry residue is not required.

6. A composition according to claim 1 wherein the ratio of PVAlc:benzalkonium chloride is 1:2 or greater if a dry residue is not required.

7. A composition according to claim 1 wherein the benzalkonium chloride is present in an amount of 0.2 to 12% (w/w).

8. A composition according to claim 1 wherein the PVAlc is present in an amount of 0.5 to 30% (w/w).

9. A composition according to claim 1 wherein the peroxide is present in an amount less than 15% w/w.

10. A composition according to claim 1 wherein the peroxide is present in an amount of 5 to 7%.

11. A composition according to claim 1 wherein the peroxide is present in an amount of 1.0 to 3%.

12. A composition according to claim 1 wherein the alcohol has a boiling point of 97° C. or below.

13. A composition according to claim 1 wherein the alcohol is selected from the group consisting of ethanol, isopropanol, and propanol.

14. A composition according to claim 1 wherein said composition is free from amines.

15. A composition which is bactericidal, fungicidal and viricidal when applied, consisting essentially of a combination of polyvinyl alcohol-benzalkonium chloride complex, hydrogen peroxide, and a carrier consisting of water, an alcohol and optionally glycols, fragrances and colorants wherein the amount of hydrogen peroxide is in the range of 1.0% to 3% w/w.

16. A composition according to claim 15 wherein the alcohol has a boiling point of 97° C. or below.

17. A composition according to claim 15 wherein the alcohol is selected from the group consisting of ethanol, isopropanol, and propanol.

18. A composition according to claim 15 wherein said composition is free from amines.

* * * * *